United States Patent
Armentrout

(10) Patent No.: US 7,691,988 B2
(45) Date of Patent: Apr. 6, 2010

(54) DNA IN THE PRESENCE OF GELLAN

(75) Inventor: Richard W Armentrout, Decatur, IL (US)

(73) Assignee: Shin-Etsu Chemical Company, Ltd., Tokyo (JP)

( * ) Notice: Subject to any disclaimer, the term of this patent is extended or adjusted under 35 U.S.C. 154(b) by 770 days.

(21) Appl. No.: 10/718,488

(22) Filed: Nov. 20, 2003

(65) Prior Publication Data

US 2004/0203114 A1 Oct. 14, 2004

Related U.S. Application Data

(60) Provisional application No. 60/427,987, filed on Nov. 20, 2002.

(51) Int. Cl.
*C07H 21/04* (2006.01)
(52) U.S. Cl. ............ 536/23.1; 536/123; 204/469; 435/178
(58) Field of Classification Search ........... 536/23.1, 536/123; 204/469; 435/178
See application file for complete search history.

(56) References Cited

U.S. PATENT DOCUMENTS

| 5,143,646 A | 9/1992 | Nochumson et al. ...... 252/315.3 |
| 5,616,478 A | 4/1997 | Chetverin et al. ........ 435/91.2 |
| 6,203,680 B1 | 3/2001 | Cole ................... 204/469 |

FOREIGN PATENT DOCUMENTS

WO 02/02587 A1 1/2002

OTHER PUBLICATIONS

Greisen, K et al. PCR primers and probes for the 16S rRNA gene of most species of pathogenic bacteria, including bacteria found in cerebrospinal fluid. Journal of Clinical Microbiology. Feb. 1994. 32(2): 335-351.*

Chetverina, H.V. et al., "Molecular Colony Diagnostics: Detection and Quantitation of Viral Nucleic Acids by In-Gel PCR," *BioTechniques*, 33(1):150-156, Jul. 2002.

Cohen, D.M., "The Polymerase Chain Reaction," in Ausubel et al.,(eds.), *Current Protocols in Molecular Biology*, John Wiley & Sons, Inc., Chapter 15, Sections 1-8, 2003.

Cole, K.D., "Reversible Gels for Electrophoresis and Isolation of DNA," *BioTechniques*, 26(4):748-756, Apr. 1999.

Cole, K.D. et al., "Modification of the Electrokinetic Properties of Reversible Electrophoresis Gels for the Separation and Preparation of DNA," *Applied Biochemistry and Biotechnology*, 82:57-76. 1999.

Doner, L.W. and Bécard, G., "Solubilization of Gellan Gels by Chelation of Cations," *Biotechnology Techniques*, 5(1):25-28, 1991.

Gibb, A.P. and Wong, S., "Inhibition of PCR by Agar from Bacteriological Transport Media," *Journal of Clinical Microbiology*, 36(1):275-276, Jan. 1998.

Mitra, R. D. and Church G. M., "In situ localized amplification and contact replication of many individual DNA molecules," *Nucleic Acids Research*, 27(24)e34:i-vi, 1999.

Moss, M. Jr., "Isloation of Proteins for Microsequence Analysis," in Ausubel et al.,(eds.); *Current Protocols in Molecular Biology*, John Wiley & Sons, Inc., Chapter 10.19, p. 9, 2003.

Rath, P-M and Schmidt, D., "Gellan gum as a suitable gelling agent in microbiological media for PCR applications," *Journal of Medical Microbiology*, 50(1):108-109, Jan. 2001.

Yamaguchi, Y. et al., "Inhibitory Effects of Agarose Gel and LB Medium on DNA Sequencing," *BioTechniques*, 33(2):282 & 284, Aug. 2002.

* cited by examiner

*Primary Examiner*—Leon B. Lankford
*Assistant Examiner*—Susan E. Fernandez
(74) *Attorney, Agent, or Firm*—Seed IP Law Group PLLC

(57) ABSTRACT

A method is provided for nucleic acid amplification with enhanced sensitivity. The method for enhanced sensitivity involves carrying out the amplification reaction in the presence of gellan. For instance, the method allows for the production of detectible amounts of PCR amplified DNA from at least 10 fold fewer target molecules than a comparable PCR reaction in absence of gellan.

1 Claim, No Drawings

DNA IN THE PRESENCE OF GELLAN

CROSS-REFERENCE TO RELATED APPLICATION

This application claims the benefit of U.S. Provisional Patent Application No. 60/427,987 filed Nov. 20, 2002, where this provisional application is incorporated herein by reference in its entirety.

BACKGROUND OF THE INVENTION

1. Field of the Invention

The present invention is related to the copying or amplification of nucleic acid molecules in the presence of gellan gum.

2. Description of the Related Art

The PCR method of DNA amplification is widely used in research, forensic investigations, and medical diagnostics. PCR will amplify even a few molecules of a target DNA in a sample to the level of $10^7$ to $10^8$ molecules within a short period (1-2 hours). PCR is one of a few technologies that will detect or amplify relatively few target nucleic acid molecules. There is great interest in enhancing this ability of PCR reactions to amplify a few target nucleic acid sequences, or its "sensitivity". Many such techniques to optimize PCR reactions are described, for example, in Section 15, Vol. 3, "Current Protocols in Molecular Biology" (Edit. Ausubel, F. M., et al.), John Wiley & Sons.

For several applications of nucleic acid amplification, it is desirable to carry out the amplification within, or associated with, a gel matrix. Many types of gel material suitable for use as electrophoresis medium have been the subject of intense research as the gel is often the determining factor for a successful separation. The gels may be composed of natural materials, e.g., agarose or synthetic polymers, e.g., polyacrylamide.

When the PCR ingredients are polymerized within a polyacrylamide gel, the resulting PCR amplifications are inconsistent, perhaps due to damage to enzymes and/or nucleic acids by the free radicals necessary to polymerize the acylamide (*BioTechniques* 33(1), 150-156, 2002; Chetverina, H. V. et al. "Molecular Colony Diagnostics: detection and quantification of viral nucleic acids by in-gel PCR."; and *Nucleic Acid Research*, 27(24), e34, 1999; R. D. Mitra and G. M. Church. "In situ localized amplification and contact replication of many individual DNA molecules.").

Agarose inhibits PCR amplification when the agarose concentration is above 0.15%. (*Biotechiques* 33(2), 282-283, 2002. Yamaguchi, Y, et al "Inhibitory effects of Agarose Gel and LB medium on DNA sequencing."). Agar contains uncharacterized inhibitory components that block PCR even when present in only trace amounts in DNA purified from cells growing on the surface of agar plates. (*Journal of Clinical Microbiology* 36, 275-276, 1998 "Inhibition of PCR by agar from bacteriological transport media").

Therefore, there exists a need in the art for methods of enhanced PCR sensitivity so as to be able to amplify from samples that contain low levels of nucleic acid molecules.

BRIEF SUMMARY OF THE INVENTION

The present invention provides methods and compositions for nucleic acid amplification in the presence of gellan. The gellan may be intact or digested into small molecules.

In one aspect, the present invention provides a method for enzymatically amplifying a target nucleic acid or a fragment thereof that comprises (a) providing a nucleic acid amplification reaction mixture having a water-based liquid phase and a gellan gel matrix phase, wherein the liquid phase comprises a target nucleic acid and is entrapped in the gel matrix phase; and (b) subjecting the reaction mixture to conditions suitable for amplifying the target nucleic acid or a fragment thereof, whereby the target nucleic acid or the fragment thereof is amplified. In certain embodiments, the sample undergoing enzymatic amplification contains at least 200, 220, 240, 260, 280, 300, 400, 500, 600, 700, 800, 900,1000, 1200, 1400, 1600, 1800, or 2000 molecules of target nucleic acids. The nucleic acid amplification may be performed using PCR, LCR, TAS, NASBA, 3SR, RACE, one-sided PCR or the like. In some embodiments, the present method may further comprise the step of isolating a target nucleic acid from cells (e.g., bacterial cells) grown on gellan-containing medium.

The present invention provides methods for the amplification of nucleic acid in both purified and contaminated gellan. In one preferred embodiment, the gellan is purified using a method comprising the steps of (a) combining gellan and a DNase, where the gellan contaminated with nucleic acid, thereby providing a mixture; and (b) maintaining the mixture of (a) under conditions where the DNase degrades at least some of the nucleic acid, thereby providing purified gellan.

In another aspect, the present invention provides a method for enzymatically amplifying a target nucleic acid or a fragment thereof, comprising (a) providing a nucleic acid amplification reaction mixture that comprises a target nucleic acid, and gellan at a concentration at least or above 0.001 wt % based on the weight of water; and (b) subjecting the reaction mixture to conditions suitable fro amplifying the target nucleic acid or a fragment thereof, whereby the target nucleic acid or the fragment thereof is amplified. In certain embodiments, the amplification reaction mixture comprises gellan at a concentration at least, or above, 0.002, 0.003, 0.004, 0.005, 0.006, 0.007, 0.008, 0.009, 0.01, 0.011, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.25, 0.3, 0.35, or 0.4 wt % based on the weight of water.

The present application also provides composition suitable for use in nucleic acid amplification comprising gellan at a concentration at least or above 0.001 wt % based on the weight of water, DNA polymerase, dNTPs, a target nucleic acid, and water. In certain embodiments, the present composition comprises gellan at a concentration at least, or above, 0.002, 0.003, 0.004, 0.005, 0.006, 0.007, 0.008, 0.009, 0.01, 0.011, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.25, 0.3, 0.35, or 0.4 wt % based on the weight of water.

BRIEF DESCRIPTION OF THE SEQUENCE IDENTIFIERS

SEQ ID NO:1 is the nucleotide sequence for the forward primer used in the amplification of the β-galactosidase Z subunit gene.

SEQ ID NO:2 is the nucleotide sequence for the reverse primer used in the amplification of the β-galactosidase Z subunit gene.

DETAILED DESCRIPTION OF THE INVENTION

Gellan gum is a bacterial (*Sphingomonas elodea*) exopolysaccharide consisting of tetra-saccharide repeating units:

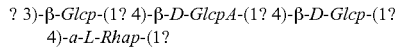
4)-a-L-Rhap-(1?

Both the native and the de-acylated Gellan polymers will form gels when dilute solutions are heated and cooled in the presence of cations.

Gellan has several properties that may make it an attractive polymer to use in place of other gel systems, such as agar, agarose or polyacrylamide, for gel-phase PCR applications:

1) Gellan forms gels at relatively low temperatures. This allows PCR enzymes and DNA to be mixed without damage with soluble gellan before gel formation.

2) Once gellan has solidified into a gel, the gel is stable even at temperatures approaching 100° C. depending upon other gel components that are present. The PCR amplification reactions involve many cycles of rapid temperature changes, from 90° C. to 55° C. to 72° C., within minutes, for example. Gellan gels are stable under these conditions.

3) Gellan polymers will form gels using non-toxic, non-reactive cross-linking materials. Other polymers commonly used for forming gels are polymerized with reactive chemicals that can damage enzymes and biological materials. For example, acrylamide gels are polymerized by a free-radical process that damages biological materials, and the gels contain large amounts of un-reacted monomers that are both toxic and damaging to proteins (*Current Protocols in Molecular Biology*, Vol 2, 10.19.9, Malcom Moos, Wiley Interscience).

4) Gellan gels are exceptionally clear. This clarity allows for the detection of PCR amplification products within the gel matrix by the use of fluorescent dyes, such as Syber green. Syber green, and related fluorescent dyes, have little or no fluorescence in solution but bind specifically to double-stranded DNA. They are highly fluorescent in the bound state. It is possible to diffuse the Syber green into the gellan matrix after PCR amplification, or, alternatively, to carry out the PCR amplification in the presence of the dye. Plastic or glass PCR reaction containers (tubes or chambers having glass slides, for example) that allow for the passage of light in the visible range are commonly used for PCR reactions. The visible light passes through the reaction container and the clear gellan matrix and excites the Syber green bound to the amplified DNA, causing fluorescence. By these methods, due to the clarity of the gellan matrix, it is possible to quantitatively detect the amount of PCR-derived DNA amplification within the gel matrix without opening the reaction container.

Despite these advantages, gellan is an unlikely candidate for addition to PCR reactions, as the intact gellan polymer sequesters $Mg^{2+}$ as cross-linking ions for gel formation. For example, a standard gellan gel for microbial growth is formed with about 0.75% gellan and 0.1% $MgSO_4$, and such a gel may be solubilized by incubation with chelation agents (10 mM citrate, for example) that sequester the $Mg^{2+}$ ions (*Biotechnology Techniques* 5(1), 25-28, 1991. Doner, L. W. and G. Bécard. "Solubilization of gellan gels by chelation of cations"). PCR reactions absolutely depend upon $Mg^{2+}$ for activity. Therefore, it seemed unlikely that PCR reactions could proceed in the presence of a large excess of polymer that tightly binds $Mg^{2+}$. The present inventors have surprisingly discovered that PCR can be conducted in the presence of gellan.

Definitions

For purposes of the present invention, the following terms have the indicated meanings.

The term "amplification" refers to the making of one or more copies of a target nucleic acid or a fragment thereof.

A "polynucleotide amplification reaction" is a template-dependent in vitro enzyme-catalyzed reaction for increasing the number of target polynucleotides.

A "nucleic acid amplification reaction mixture" refers to a mixture comprising the components necessary for nucleic acid amplification, such as dNTPs, water, a target nucleic acid, and a polymerase. Depending on methods for nucleic acid amplification, the necessary components may differ. For example, ligase chain reactions require the presence of a ligase, which may not be needed in certain polymerase chain reactions.

In certain embodiments, a nucleic acid amplification reaction mixture further comprises gellan, either in a liquid form (e.g., gellan suspension or gellan solution), or in a gel form (i.e., gellan gel matrix).

A liquid phase is entrapped within a gel matrix phase when the gel matrix has a highly expanded surface that penetrates the liquid phase, so that the liquid phase is substantially motionless (i.e., not be able to move from one location to another in the gel matrix).

The term "sensitivity" refers to the level of target nucleic acid sequences capable of being amplified. For the purposes of the present invention, the term "enhanced sensitivity" refers to the ability to amplify lower levels of nucleic acid molecules in the presence of gellan than in the absence of gellan.

The term "biomolecules" includes nucleic acids such as DNA and RNA, oligonucleotides, peptides, proteins, and other biological materials commonly separated using electrophoresis techniques.

The term "contaminated" refers to commercial or untreated gellan gum that contains nucleic acid in mixture with the gellan. Commercially available gellan has about 20-30 ppm nucleic acid. For example, KELCOGEL® gellan has about 24 ppm nucleic acid, KELCOGEL F® gellan has about 20 ppm nucleic acid, and GELRITE® gellan has about 28 ppm, where these values are obtained by measuring the absorbance at 260 nm, i.e., the $OD_{260}$ value, as measured on a spectrophotometer using a 0.5 wt % aqueous gellan solution, and calculating nucleic acid concentration using the Warburg-Christian calculation method. The Warburg-Christian method is described in O. Warburg and W. Christian (1942) Biochem. Z. 310:384-424, and entails measurement of absorbance ratios at 260 nm and 230 nm, and again at 260 nm and 280 nm. Background correction is made using absorbance values at 320 nm, taking into consideration the factors outlined by Warburg & Christian.

The term "purified" refers to treated gellan gum containing less than 10 ppm nucleic acid (based on weight parts of gellan), preferably less than 5 ppm, and more preferably less than 1 ppm.

The terms "cross-linking agent" or "cross-linker" refers to an additive which induces or promotes the association of the intertwined gellan molecules in solution, resulting in gel formation. Controlled changes in the chemical or physical structure of the cross-linking agent may revert the gel into liquid solution. Examples of cross-linking agents are divalent cations and diamines, including diamines containing disulfide bonds.

The term "cystamine" refers to cysteine dimethyl ester. Cystamine contains both diamino groups and disulfide bond, and is used as a cross-linker for the gellan gel formation.

The term "degradation" refers to depolymerization of an oligonucleotide. Degradation of an oligonucleotide will generally occur through enzymatic hydrolysis of internucleotide phosphodiester bonds to release short oligonucleotides and/or mononucleotides.

The term "divalent metal cation" refers to divalent group IIA cations such as $Ca^{2+}$, $Mg^{2+}$, $Sr^{2+}$, $Ba^{2+}$, etc. and to divalent transition cations such as $Zn^{2+}$, $Mn^{2+}$, $Cu^{2+}$, etc.

The term "diamine" refers to organic compounds having two amine groups such as ethylene diamine, and 1,3 diamino-2-hydroxypropane (DAHP), etc. The term "polyamine" refers to organic compounds having two or more amine groups. A suitable polyamine is a star-shaped dendrite in which there are amino groups at the end of the arms of the star. Typically, the amine groups of a diamine or polyamine are separated from each other by a hydrocarbon or hydrocarbon derivative chain.

The term "disulfide" refers to the groups containing —S—S— bond. An example of a compounds containing disulfide bond is a cystamine.

The term "DNase" refers to any enzyme that degrades DNA.

The term "DNase activating agent" refers to any additive to the gellan purification process wherein the speed and/or completeness of the degradation of the nucleic acid contaminate in gellan is enhanced as compared to the same process in the absence of such an agent. An example of the "DNase activating agent" is sodium azide.

The terms "electroosmosis" and "electroosmotic flow" refer to the movement of a charged substance through a membrane by the way of an electric field—induced convective flow.

The term "electrophoretic mobility" refers to the steady-state velocity induced per unit field strength for a selected biomolecule during electrophoresis. Electrophoretic mobility can measured in terms of the required for a biomolecule to pass a particular point in the gel, or in terms of a distance of a molecular species from a reference point along the length of the gel at a selected time.

The term "gellan gum" or "gellan" refers to a family of related carbohydrate polymers produced by *Sphinogomonas* bacteria (previously identified as *Pseudomonas*) and would include gellan gum produced by genetically engineered bacteria and chemically modified gellan gums.

The term "nucleic acid" or "oligonucleotide" refers to a polymeric form of nucleotides at least 5 bases in length. The nucleotides of the invention can be deoxyribonucleotides, ribonucleotides, or modified forms of either nucleotide.

The term "polypeptides" refers to molecules including at least two linked amino acids and derivatives thereof.

The term "reducing agent" refers to any agent which can effect the reduction of a disulfide bond of a cross-linking agent, thereby breaking the bond, without effecting a chemical change on any other substitutents on the cross-linking agent. An example of the reducing reagent is dithiothreitol (DTT).

The term "reversibility" is used to refer to the ability of gellan gels to be returned to a liquid state.

The term "size-separation property modifying polymer" refers to polymers that can be incorporated into the gel of the electrophoresis medium to alter the size-separation properties of the electrophoresis medium of the present invention. Examples of size-separation property modifying polymers include: hydroxyethyl cellulose, dextran, ficoll, poly(alyleneoxide), polyacrylamide, etc.

The term "zone" or "band" refers to a portion of an electrophoresis medium or gel that contains substantially one biological material. Depending on the purity desired in a particular application of the present invention, there may be some degree of other biomolecules using the method of the present invention.

Description

The present invention provides novel methods for amplifying or copying nucleic acid molecules in the presence of gellan, and thereby enhancing the sensitivity of the amplification or copying of the nucleic acid molecules.

As discussed above, gellan gum is a linear carbohydrate polymer produced by bacterial fermentation as described in U.S. Pat. Nos. 4,326,052; 4,377,636; 4,385,123 and European Patent No. 0 012 552, the entire disclosure and contents of which are hereby incorporated by reference. The carbohydrate polymer consists of repeating tetrasaccharide units composed of two glucose sugars, a rhamnose and a glucuronic acid. This structure is described more completely in O'Neil et al., "Structure of the Acidic Polysaccharide by *Pseudomonas elodato*" in *Carbohydrate Research* (1983), 124, 123-133 and Jansson et al, "Structural Studies of Gellan Gum, an Extracellular Polysaccharide Elaborated by *Pseudomonas elodato*" in *Carbohydrate Research* (1983), 124, 135-139. The gellan gum produced by typical fermentation means has both O-acetyl and O-L-glyceryl 3-linked to glucose units. The acetyl groups can be removed during processing and the resulting materials are called low acyl gellan gums as described in Sanderson, Food Gels, P. Harris (ed.) Elsevier Applied Science, (New York: 1990), 202-232. Commercially available low acyl gellan gums are available under the tradenames KELCOGEL™, GELRITE™ and PHYTAGEL™ gellan.

Gellan has a number of unique properties that make it a desirable medium for electrophoresis and a potential replacement for agarose as one of the most widely used electrophoresis gels. In the presence of a cross-linking agent, gellan gum forms strong gels in a range of polymer concentrations and buffer compositions. Accordingly, these gels are suitable for high-resolution electrophoresis and the subsequent recovery of the separated biomolecules. Gellan based gel has the additional advantage of being "reversible" in that the gel can be returned to a liquid state under relatively mild conditions, typically by sequestering or chemically altering the cross-linking agent. Furthermore, gellan forms gel at substantially lower concentration than agarose. Electrophoresis gels having gellan contents of as low as 0.03 wt % may be constructed. In contrast, agarose gel formation typically requires the presence of 0.8%-3 wt % agarose. Particularly when gel electrophoresis is followed by recovery of the separated biomolecules, it is advantageous to use a minimum amount of gellant (e.g., agarose, gellan) so that there is less gellant that needs to be separated from the recovered biomolecule.

Gellan may be used to form a gel for electrophoretic separation of biomolecules. In general, a typical gellan concentration for casting electrophoresis gel is approximately 0.1-0.5 wt %. Gellan is commercially available in both solid and liquid forms, and either of these forms may be used in the practice of the present invention. In one aspect, solid gellan is combined with water to create a suspension of the gellan in water. This suspension is conveniently created by combining about ca. 2 or less grams of solid gellan with ca. 100 grams of water so as to provide an aqueous suspension having about 2 wt % or less gellan. When the concentration of gellan in the suspension is greater than about 2 wt %, then the suspension tends to be lumpy and non-uniform due to non-uniform wetting of the particulate gellan, where this consistency is less amenable to action by DNase. The water that is used to prepare the gellan suspension is preferably deionized or distilled water, however, any water may be used.

In order to expedite formation of the suspension, the gellan water mixture is preferably maintained at slightly elevated temperature, e.g., 35-40° C. for approximately 2 hours with agitation. When higher temperature is used, the gellan tends to dissolve in the water rather than form a suspension in the water. In those instances where it is desired to use a nucleic acid-free gellan, or at least to use a gellan that has a reduced level of nucleic acid compared to commercially available gellan, the solution of gellan may be combined with DNase. The DNase degrades the nucleic acid (a polynucleotide) into mononucleotides, where the mononucleotides will not complex with the fluorescent dye and will not provide a fluorescent signal. In such a case, it is observed that DNase tends to degrade nucleic acid more slowly in a gellan solution than in a gellan suspension. A gellan solution is also somewhat disadvantageous in that it tends to be more viscous that a gellan suspension at the same gellan concentration. In a gellan solution, a gellan concentration of less than 2 wt %, e.g., 0.5 wt %, is generally preferred in order to create a solution that has a convenient viscosity. While temperatures of less than 37° C. may be used to form the gellan suspension, it is observed that a uniform suspension tends to form more slowly as the temperature is reduced much below about 37° C. While agitation for about 2 hours is typically adequate to create a uniform-appearing aqueous gellan suspension, either longer or shorter times may be used. Longer agitation times tend to allow more of the gellan to dissolve in the water, with a concomitant increase in viscosity. Shorter agitation times do not always allow all of the gellan particles to wet and become suspended in the water. When removal of nucleic acid is desired, the mixture of gellan and DNase is maintained at 30-45° C. for at least 0.5 hour, more typically at least 1 hour, and still more typically at least 2 hours.

In addition to the DNase, a DNase activating agent may be added to the water/gellan mixture to enhance the speed of DNase degradation of the nucleic acid contaminant. DNase activating agents are known in the art, where an example of a DNase activating agent is sodium azide. As one means for adding to the DNase activating agent to the water/gellan mixture, it is convenient to prepare a solution of the DNase activating agent, and then some of that solution to the water/gellan/DNase mixture. For instance, sodium azide may be prepared as a 5 wt % solution in water, and then a sufficient amount of this solution is added to the water/gellan/DNase mixture to provide a sodium azide concentration of about 1-5 mM, e.g., 3 mM.

The extent of the degradation process can be monitored by taking small samples of the mixture and staining them with ethidium bromide followed by observing the fluorescence of the sample. An ethidium bromide concentration of about 0.5 mM is suitable. The purification is at least partially complete when there is reduced background fluorescence observed in the sample. Another approach is to monitor the optical density of a sample of gellan suspension, where the absorbance at 260 nm is directly proportional to the concentration of nucleic acid in the suspension. For this procedure it is necessary to precipitate the sample with iso-propanol or ethanol, then dry and resuspend the sample. For example, a 0.25 wt % gellan suspension in water, prior to addition of DNase, may have an $OD_{260}$ of about 0.6, which corresponds to a nucleic acid concentration of about 0.30 μg/ml solution, or 24 ppm nucleic acid based on weight parts of gellan. Note that these numbers are based on $A_{260}=1$ at 50 μg/mL of nucleic acid. Over the course of about 2 hours at 37° C. in the presence of 5 units DNase/mL solution, the $OD_{260}$ drops to a level that corresponds to a nucleic acid concentration of less than 0.05 μg DNA/mL solution, or in other words, less than 1 ppm nucleic acid based on weight parts of gellan. This procedure is conveniently used for determining times and concentrations needed to optimize the nucleic acid degradation reaction. It is not needed to prepare gellan for use in DNA electrophoresis.

In general, any reduction in nucleic acid contamination of gellan is desirable because this reduction means that there is less background noise created when the gellan is used in an electrophoresis gel, and a nucleic acid intercalating agent is used to visualize the resolved nucleic acid. In one aspect of the invention, at least half of the nucleic acid initially present in contact with the starting gellan is degraded by the DNase. In other words, if the starting gellan is contaminated with x wt % nucleic acid, and the purified gellan is contaminated with y wt % nucleic acid, then x/y is less than 0.5.

Commercial gellan typically has greater than 10 ppm nucleic acid contamination, and more typically has greater than 20 ppm nucleic acid contamination. The PCR reaction of the present invention may be conducted in the presence of gellan that contains nucleic acid at a concentration of greater than 20 ppm. Alternatively, the nucleic acid content of the gellan can be reduced as described above, using DNase.

As described above, the present invention provides methods for nucleic acid amplification in the presence of gellan. Gellan may be in a nucleic acid amplification reaction mixture in a liquid form (e.g., gellan suspension, and gellan solution) or in a gel matrix form (e.g., gellan gel). In addition, gellan may be intentionally added to the reaction mixture to increase the sensitivity of the nucleic acid amplification reaction. Alternatively, gellan in a nucleic acid amplification reaction mixture may be originated (carried over) from a source where a target nucleic acid is obtained. For instance, gellan may be originated from a gellan-containing culture medium for cells from which a target nucleic acid is isolated, or from a gellan gel in which a target nucleic acid is separated via electrophoresis.

In the embodiments where gellan is present in a nucleic acid amplification reaction mixture in a gel matrix form, the reaction mixture may be prepared by providing a solution containing all the components of the amplification reaction mixture (which may include a cross-linker for forming gellan gel) except gellan, and another solution containing gellan. The mixing of the two solutions results in the formation of gellan gel matrix in which the other components of the reaction mixture are entrapped. In certain embodiments, the two solutions may be heated briefly (e.g., at 55° C. for 15 seconds) to facilitate uniform distribution of the other components of the amplification reaction mixture in the gellan gel matrix. The resulting amplification reaction mixture allows in situ nucleic acid amplification. In other words, the amplification products would be entrapped in the gellan gel matrix locally.

Many template-dependent processes are available to amplify a nucleic acid target sequence of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably, reverse transcription and PCR™ amplification procedures may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA), and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic*. 1:111-19, 1991) and walking PCR (Parker et al., *Nucl. Acids. Res*. 19:3055-60, 1991). Other methods employing amplification may also be employed to obtain a full length cDNA sequence.

The following examples are set forth so as to provide those of ordinary skill in the art with a complete disclosure and description of how to make and use the subject invention, and are not intended to limit the scope of what is regarded as the invention.

EXAMPLE 1

PCR Amplification is not Inhibited in the Presence of Gellan

To determine if PCR amplification is effected by the presence of intact gellan polymer molecules, or by the presence of small fragments of the gellan polymer, gellan polymer or gellan fragments were mixed with a test DNA and the resulting sample amplified using PCR. The results were compared to the PCR amplification of the same DNA in the absence of gellan or its fragments.

These experiments were performed using the following experimental protocol:

Template DNA

The test DNA was plasmid L430 DNA that was linearized by cleavage with Xmn I. The DNA (17.2 pg/µl) was mixed with a 400-fold excess of soluble gellan (7.0 ng/µl) or the same concentration of gellan digested to small fragments by gellanase (U.S. Pat. No. 5,342,773). PCR amplification was performed on the samples.

Linear DNA of plasmid pL430 ("L430") was used as a test PCR template. This plasmid has about 1.2 kb of DNA (from *Sphingomonas* sp. S7) inserted into the MCS region of the parent plasmid pBluescript II (KS-) ("pBS"), between the annealing sites for the primers described below. The insert DNA was unusually GC-rich (72%), making it a challenging target sequence for PCR amplification. The amplified region is the 1.2 kb pairs plus an additional 0.2 kb attributed to the primers.

The L430 retains the unique Xmn I site in pBS within the amp gene which is a convenient site to cut to convert the plasmid DNA to a linear form.

Linear Target DNA, L430

Purified L430 DNA was diluted to a concentration of 200-250 ng/µl and was digested with Xmn I. Dilutions of the cut DNA were analyzed by gel electrophoresis. The Xmn I cut L430 DNA ran as a major band on gel electrophoresis with the 4 kb marker, as expected for a linear DNA of 4.1 kb.

The reaction mixture containing the linear DNA was then diluted to about 0.5 ng/µl. This solution became the stock solution of template DNA for PCR amplification.

PCR Primers

The forward primer was is a 17 base single-stranded DNA that hybridizes to the "sense" strand of the β-galactosidase Z subunit gene with the 3' OH at base #617 on the pBS map:

5'-*GTAAAACGACGGCCAGT*-3'   (SEQ ID NO:1)

This primer has a calculated Tm of 52° C.

The reverse primer is a 19 base single-stranded DNA that hybridizes to the "anti-sense" strand of the β-galactosidase Z subunit gene with the 3' OH at base #814 on the pBS map:

5'-*CGAAACAGCTATGACCATG*-3'   (SEQ ID NO:2)

This primer has a calculated Tm of 56° C.

The primers were combined together in equal molar concentrations and diluted to a final concentration of 5 µM and stored frozen.

DNA Polymerases

A mixture of the heat-stable Taq DNA polymerase and a heat-stable 3'-5' exonuclease-containing Pfu polymerase were used (Epicentre). One unit of activity converts 10 nM of dNTP to DNA in 30 minutes at 74° C.

Thermal Cycler Robot Programming

The reaction ingredients are all held on ice, mixed and held on ice, and then transferred from the ice temperature immediately to the denaturation temperature. The first amplification cycle has an extended time for denaturation (2 minutes). An automatic thermocycler was programmed using the following "hot start" amplification cycle:

| Cycle 1 | denaturation | annealing | amplification |
|---|---|---|---|
| Temperature | 94° C. | 55° C. | 72° C. |
| Time | 2 min | 45 sec | 1 min 30 sec |
| Cycles 2-38 | denaturation | annealing | amplification |
| Temperature | 94° C. | 55° C. | 72° C. |
| Time | 45 sec | 45 sec | 1 min 30 sec |
| Final Cycle | amplification | Storage/end | |
| Temperature | 72° C. | 6° C. | |
| Time | 10 min | hold | |

Determination of Optimal $Mg^{2+}$ and Enhancer Ingredients

The Failsafe PCR premix selection kit (Epicentre) was used to determine the optimal ion and enhancer combination for this template DNA. The 12 separate PCR reaction mixtures were prepared as described by the supplier ($Mg^{2+}$ concentrations varied from 1.5 mM to 4.0 mM and enhancer amounts from 0 to 4x). The final PCR reactions contained 50 mM Tris-HCL, pH 8.3; 50 mM KCl; 200 μM of each dNTP. The best results were obtained using premix G, and this mixture was used for the remainder of the PCR reactions.

PCR Amplifications

PCR amplification was done on pure L430 DNA that was not mixed with either the gellan polymer or the gellanase-produced gellan fragments (sample 1); DNA mixed with soluble intact gellan polymer (sample 2); or DNA mixed with gellanase-produced gellan fragments (sample 3). A master mixture was prepared for the 3 PCR reactions. The final volume was 69 μl and included the stock primers (200 nM final concentration), the enzyme mixture (1.25 units/reaction), and water. The mixture was prepared from cold ingredients and the final mixture was held on ice.

Three separate thin-walled 600 μl tubes were prepared. To each reaction tube was added 25 μl of pre-mix solution G containing $Mg^{2+}$, the four dNTPs, and enhancers. The DNA samples were added. 23 μl of master mixture was added to each tube on ice. The tubes were transferred from ice to initiate PCR.

An aliquot (10 μl) from each of the 3 reactions were then analyzed on S-E Gel (Shin-Etsu Bio, Inc.) by electrophoresis with 1 KB markers. Gels were run at 100v for approximately 1 hour.

Results

The target DNA was significantly amplified in all 3 DNA samples, with no apparent differences between band intensities. These data demonstrate that it is possible to PCR-amplify DNA in the presence of a 400+ fold excess of soluble gellan polymer.

EXAMPLE 2

PCR is not Inhibited by the Presence of High Levels of Gellan

To test the ability of PCR to occur from within the gel phase of a gellan gel, the level of 0.175% gellan was selected. Stable gels were formed with 0.175% gellan and suitable cross-linking cations, such as Mg ions. For example, 0.175% gellan gels can be used as an electrophoresis medium for the separation of DNA molecules. Limited diffusion of DNA of 100 bp or more within these gels allows for the formation and maintenance of sharp bands according to the size of the DNA (Cole, K D. "Reversible gels for electrophoresis and isolation of DNA. BioTechniques 26, 748-756, 1999).

The PCR ingredients were the same as described in Example 1, except where noted. All ingredients and solutions were held on ice before addition to the PCR thin-walled tubes. The reaction mixtures were held on ice until the thermal steps described below. The reactions were set up as follows, in order of addition:

| | Tube # | | | | | |
|---|---|---|---|---|---|---|
| | 1' | 2' | 3' | 4' | 5' | 6' |
| Water (μl) | 10.5 | 10.5 | 12.5 | 14.5 | 10.5 | 10.5 |
| Primer (μl of 5 μM each) | 2.0 | 2.0 | 2.0 | 0.0 | 2.0 | 2.0 |
| Enzyme(μl) | 0.5 | 0.5 | 0.5 | 0.5 | 0.5 | 0.5 |
| (stock solution: 0.5 ng/μl L430 linear DNA) | 2.0 | 2.0 | 0.0 | 0.0 | 2.0 | 2.0 |
| 2 × pre-mix G (Epicentre) | 25.0 | 25.0 | 25.0 | 25.0 | 25.0 | 25.0 |

Tubes 1'-6' were held on ice, while the following ingredients were added:

| | Tube # | | | | | |
|---|---|---|---|---|---|---|
| Ingredient (μl) | 1 | 2 | 3 | 4 | 5 | 6 |
| 5 × Gellan solution (μl) (stock solution: 0.875%) | 10 | 10 | 10 | 10 | 0 | 0 |
| Water (μl) | 0 | 0 | 0 | 0 | 10 | 10 |

The 5x gellan solution contained 0.875% PCR-grade gellan (Shin-Etsu Bio, Inc.). The stock solution was heated to 55° C. for 5 minutes before dispensing the solution to the PCR tubes. Tubes 1-6 were held at room temperature.

The reactions were set up to perform a modified "hot start" to the PCR reactions. It is known that exposure of ingredients to temperatures above 4° C. prior to initiation of PCR amplification may result in mis-amplification of primers and other problems. There are a number of methods to "hot start" the PCR reactions (such as using PCR polymerase complexed with heat-sensitive antibody, etc.). The following protocol approximates a hot start to the PCR.

Each tube of the prime tubes (1'-6') was briefly heated to 55° C. for 15 seconds (no longer) and the corresponding gellan or water-containing tubes (1-6) were also heated to 55° C. for 15 seconds at the same time. The warmed contents of the prime tubes (40 μl) were quickly transferred to the warmed gellan or water containing tubes (10 µl), mixed briefly, and placed on ice to gel. Under these conditions, the reaction mixtures containing gellan (1-4) rapidly formed gels that included all liquid in the reaction. It was not possible to remove any liquid from these gelled reaction mixtures using a micropipette.

The tubes were then placed into the automatic thermocycler and PCR reactions were performed as described in Example 1. At the conclusion of the reaction cycles, tubes 1-4 (which contained gellan) remained in the gel state, while tubes 5 and 6 contained liquid reaction solutions.

A small sample (5 µl) of each of the PCR reactions was analyzed by gel electrophoresis.

Results

Samples 5 and 6 are duplicate positive controls, and strong PCR amplification in the absence of gellan was seen in both reactions. Samples 3 and 4 were negative controls lacking target DNA (3) or lacking both target DNA and primers 4). No bands of amplified DNA were observed in these reactions. Samples 1 and 2 were experimental reactions of PCR from mixtures in the gel state. Strong and specific PCR amplification of the target DNA was observed to levels comparable to that of the positive controls.

These findings demonstrate that it is possible to PCR-amplify DNA from within a reaction mixture gelled with a gellan polymer.

EXAMPLE 3

The Presence of the Gellan Polymer Enhances the Sensitivity of the PCR DNA Amplification To determine the effect of gellan gel on the sensitivity of PCR nucleic acid amplification, PCR amplification of target DNA sequences at various concentrations was carried out in the presence and absence of gellan gel.

The PCR ingredients were the same as in Example 1, except where noted. All ingredients and solutions were held on ice before addition to the PCR thin-walled tubes. The reaction mixtures were held on ice until the thermal steps described below. The reactions were set up as follows, in order of addition:

|  | Tube # | | | | |
| --- | --- | --- | --- | --- | --- |
|  | 1' | 2' | 3' | 4' | 5' |
| Water (µl) | 10.5 | 10.5 | 10.5 | 10.5 | 10.5 |
| Primer (µl:5 µM each) | 2.0 | 2.0 | 2.0 | 2.0 | 2.0 |
| Enzyme(µl) | 0.5 | 0.5 | 0.5 | 0.5 | 0.5 |
| DNA(L430 linear DNA) | $2.2 \times 10^8$ | $2.2 \times 10^6$ | $2.2 \times 10^4$ | $2.2 \times 10^2$ | 0.0 |
| 2 × pre-mix G (Epicentre) | 25.0 | 25.0 | 25.0 | 25.0 | 25.0 |

Tubes 1'-5' were held on ice.

|  | Tube # | | | | |
| --- | --- | --- | --- | --- | --- |
|  | 1 | 2 | 3 | 4 | 5 |
| 5 × Gellan solution (µl) (stock solution: 0.875%) | 10 | 10 | 10 | 10 | 10 |

The 5× gellan solution contained 0.875% PCR-grade gellan (Shin-Etsu Bio, Inc.). The stock solution was heated to 55° C. for 5 minutes before dispensing the solution to the PCR tubes. Tubes 1-5 were held at room temperature.

|  | Tube # | | | | |
| --- | --- | --- | --- | --- | --- |
|  | 6 | 7 | 8 | 9 | 10 |
| Water (µl) | 20.5 | 20.5 | 20.5 | 20.5 | 20.5 |
| Primer (µl) (5 µM each) | 2.0 | 2.0 | 2.0 | 2.0 | 2.0 |
| Enzyme(µl) | 0.5 | 0.5 | 0.5 | 0.5 | 0.5 |
| DNA(molecules) (L430 linear DNA) | $2.2 \times 10^8$ | $2.2 \times 10^6$ | $2.2 \times 10^4$ | $2.2 \times 10^2$ | 0.0 |
| 2 × pre-mix G (Epicentre) | 25.0 | 25.0 | 25.0 | 25.0 | 25.0 |

Each tube of the prime tubes (1'-5') were mixed with the gellan polymer and PCR was initiated as a modified "hot start" as described in Example 2 in tubes 1-5. In the case of the reactions without gellan matrix (tubes 6-1), the PCR ingredients were held on ice and the mixtures in the reaction tubes were also held on ice.

The tubes (1-10) were then placed into the automatic thermocycler and PCR reactions were performed essentially as described in Example 1. At the conclusion of the reaction cycles, tubes 1-5 remained in the gel state.

A sample of each of the PCR reactions was analyzed by gel electrophoresis (5 µl of reactions 1 and 6; 20 µl of reactions 2-5 and 7-10).

Results

Strong PCR amplification was seen in reactions carried out with PCR ingredients within gellan gels that contained the target DNA (samples 1-4). The amplified DNA was the expected size for full-length copies from the provided primers (about 1.3-1.4 kb). In the presence of the gellan gel matrix, measurable amounts of amplified DNA were produced with about 220 target molecules in the PCR reaction mixture (sample 4).

By contrast, in the conventional PCR reaction mixtures, amplified DNA was detected in samples 6-8 but not in 9 or 10. Under comparable conditions, the conventional PCR is able to produce measurable amounts of amplified DNA with about 22,000 initial target DNA molecules. The presence of the gellan polymer enhances the sensitivity of the PCR DNA amplification.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A nucleic acid amplification reaction mixture for use in nucleic acid amplification of enhanced sensitivity, comprising water, gellan at a concentration above 0.005 wt % based on the weight of water, a DNA polymerase, dNTPs, and a target nucleic acid, wherein the nucleic acid amplification reaction mixture is capable of amplifying a lower level of the target nucleic acid when gellan is present than can be amplified when gellan is absent.

* * * * *

SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Forward primer

<400> SEQUENCE: 1
gtaaaacgac ggccagt                                                17

<210> SEQ ID NO 2
<211> LENGTH: 19
<212> TYPE: DNA
<213> ORGANISM: Artificial Sequence
<220> FEATURE:
<223> OTHER INFORMATION: Reverse primer

<400> SEQUENCE: 2
cgaaacagct atgaccatg                                              19